Figure 1:
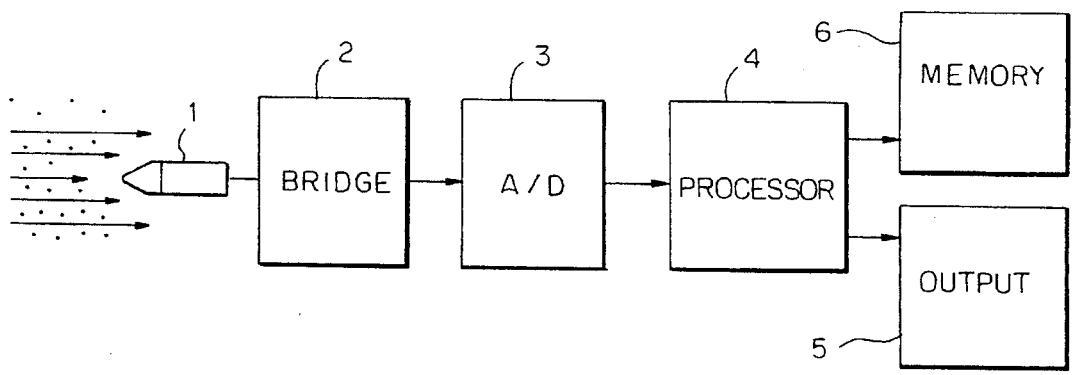

United States Patent [19]

Hauf

[11] Patent Number: 5,567,865

[45] Date of Patent: Oct. 22, 1996

[54] METHOD FOR DETERMINING THE SIZE OF AIRBORNE WATER DROPLETS

[75] Inventor: Thomas Hauf, Seefeld, Germany

[73] Assignee: Deutsche Forschungsanstalt für Luft-und Raumfahrt e.V., Köln, Germany

[21] Appl. No.: 528,494

[22] Filed: Sep. 14, 1995

[30] Foreign Application Priority Data

Sep. 14, 1994 [DE] Germany .................. 44 32 714.5

[51] Int. Cl.$^6$ ............................................. G01N 37/00
[52] U.S. Cl. .................. 73/28.01; 73/170.17; 73/204.14
[58] Field of Search ........................... 73/53.01, 64.52, 73/170.17, 170.18, 170.19, 204.14, 204.15, 204.18

[56] References Cited

U.S. PATENT DOCUMENTS

| | | | |
|---|---|---|---|
| 2,702,471 | 2/1955 | Vonnegut | 73/28 |
| 2,740,293 | 4/1956 | Brady | 73/170.19 |
| 4,446,721 | 5/1984 | Bruce et al. | 73/29 |
| 4,744,246 | 5/1988 | Busta | 73/204 |
| 4,807,151 | 2/1989 | Citron | 364/510 |
| 4,884,440 | 12/1989 | Berthel | 73/170 |
| 4,890,494 | 1/1990 | Osbond et al. | 73/338 |
| 4,936,144 | 6/1990 | Djorup | 73/189 |
| 5,056,047 | 10/1991 | Sondergeld | 364/556 |
| 5,261,538 | 11/1993 | Evans et al. | 209/2 |
| 5,263,369 | 11/1993 | Cutler | 73/204.15 |

*Primary Examiner*—Hezron E. Williams
*Assistant Examiner*—Jay L. Politzer
*Attorney, Agent, or Firm*—Browdy and Neimark

[57] ABSTRACT

To determine the size of airborne water droplets having a diameter from approximately 1 to 100 μm, if such water droplets move at a velocity of 50 to 150 m/s relative to a measuring probe and strike it, in the probe body, whose front face toward the flow has a vapor-deposited platinum film, approximately 0.5 μm thick, whose temperature is kept constant at above 100° C. by means of a bridge circuit;

an analog voltage output signal of the bridge circuit is digitized and then further processed, with the aid of an evaluation computer program, among others, and with the aid of a formula (in accordance with equation (6)) derived from an energy balance for a droplet striking a platinum film, determines the droplet diameter from analyzed identifying variables of a droplet signal and from other known parameters.

4 Claims, 10 Drawing Sheets

METHOD FOR DETERMINING THE SIZE OF AIRBORNE WATER DROPLETS

The invention relates to a method for determining the size of airborne water droplets. U.S. Pat. No. 2,702,471 has already disclosed a method for measuring the size of airborne particles, using a heated probe.

Airborne water droplets with a diameter on the order of magnitude of 1 to 100 μm occur in natural clouds, but also in many technical fields such as cooling towers, gas filters, atomizers, and the like. Droplets of this size can be considered spherical, so that the diameters given are equivalent to droplet masses of from 0.005 to $500 \cdot 10^{-12}$ kg. Knowing the droplet size or its distribution is of fundamental importance in learning how small cloud droplets (with a diameter from 1 to 20 μm) develop into precipitation droplets (with diameters of 500 to 1000 μm), but is also important in technical fields for monitoring and controlling processes. At present, determining the droplet size can be done only by complex optical methods. For measurements of cloud physics, for instance, laser systems made by PMS (Boulder, Colo., USA) are available; for small droplets (with diameters in the range from 0.5 to 47 μm), they use forward light scattering, and for larger droplets (with diameters in the range from 20 to 600 μm), they use optical imaging methods. However, these systems are complicated, require intensive service and upkeep, and are expensive.

In fluid mechanics, hot-film measuring systems have been used for over three decades; in principle, they comprise two components, namely a probe or sensor with a thin platinum film vapor-deposited onto a substrate body, which is why such probes are called hot-film probes, and a bridge circuit with a regulating circuit, by which the platinum film is kept at a constant temperature. The hot-film probe exists in various geometrical shapes, such as in the form of a wire, plate, cylinder, cone, wedge, and so forth. In addition to a conventional constant temperature method (CTA), there is also a constant current method (CCA), which is not intended to be used in the present case. The bridge voltage of the bridge circuit is a measure of the heat given up by the film to its surroundings. The heat transfer depends on a number of variables, such as the flow velocity, flow direction, the state of turbulence, the flow temperature, the film temperature, the density of the fluid, and so forth. This dependency has been utilized in the past, and special measuring methods based on hot films have been developed for these variables.

However, the heat transfer is affected not only by the above-discussed variables; in addition, every droplet striking the hot film draws heat from it and thus briefly changes the bridge voltage. From the signal course, an impact of the droplets can be identified clearly. Large signals can be caused only by large droplets, while small droplets produce only small signals.

The droplet has an ambient temperature of from −40° C. to 40° C., while the sensor temperature is markedly above 100° C. If the droplets are to be able to strike it, then they must move relative to the probe. Hot-film systems have been utilized in the past for droplet measurement. Hauf and Neumann-Hauf, in 1991, in DLR Mitt. 91-18, in a literature search entitled "Drop Sizing with Thermal Anemometry", put together the studies of this measurement principle that had been done and discussed the devices developed in detail; the major characteristics of the devices are listed briefly below:

V. W. Goldschmidt, M. K. Householder, "The hot-wire anemometer as an aerosol droplet size sampler", Atmospheric Environment 3, pp. 643–651, 1969:

CTA, wire, manufactured by DISA;

droplets of dibutyl phthalate, sunflower oil and Sinco prime 70;

a flow velocity of 3 m/s;

a droplet diameter of less than 200 μm; and a linear relationship between droplet size and signal maximum.

G. M. Bragg, J. Tevaarwerk, "The Effect of a Liquid Droplet on a Hot Wire Anemometer Probe" in Flow, Its Measurement and Control in Science and Industry, 1, pp. 599–603, ASME Fluids Engineering Conference, ISA, 1974:

CTA 10 μm wire, manufactured by DISA;

a flow velocity of 3 m/s and 6 m/s;

(referring to Goldschmidt and Householder, 1969:)

no unambiguous relationship between droplet size and signal maximum;

no signal characterizing variable for which an unambiguous relationship exists was found.

W. A. Burgess, P. C. Reist, "Study of Space Cabin Atmospheres", Semiannual Progress Rep. January–June 1968, Harvard School of Public Health, Boston, Mass., 1968:

CTA, 5 μm wire, manufactured by DISA;

water droplets;

a flow velocity of 0.4 m/s;

the signal maximum is dependent on the wire temperature, while the signal area is inversely dependent.

H. Medecki, M. Kaufman, D. E. Magnus, "Design Development, and Field Test of a Droplet Measuring Device" EPA-650/2-75-018, Environmental Protection Agency, Feb. 1975:

CCA, wire;

a flow velocity of ≦3 m/s;

a droplet size of 1 to 600 μm;

a concentration of <500 $cm^{-3}$;

the signal maximum is characteristic for the droplet size.

D. S. Mahler, D. E. Magnus, "Hot-Wire Technique for Droplet Measurements", American Society for Testing and Materials, Philadelphia, Pa. 19103, Special Technical Testing Publication 848, pp. 153–165, 1986:

CTA, 5 μm wire, manufactured by KLD;

droplet diameter from 40 to 280 μm;

low flow velocities;

droplet size is determined from the leading edge of the signal.

E. L. Andreas, R. M. Williams, C. A. Paulson, "Observations of condensate profiles over Arctic leads with a hot-film anemometer", Quart J. R. Met. Soc. 107, pp. 437–460, 1981:

CTA, cylindrical hot film, manufactured by DISA and TSI;

a droplet size of 10 μm;

condensate droplets over Arctic water;

analog differentiation, and linearization;

flow velocity=mean wind speed;

the signal maximum depends on the droplet size.

T. Hauf, "Messung der Wolkentropfenkonzentration mit einer Heissfilmsonde", ["Measuring Cloud Droplet Concentration with a Hot-Film Sensor"], Meteorol. Rdsch., 36, pp. 109–113, 1983:

CTA, cylindrical hot-film, manufactured by DISA;

cloud droplets;

aircraft measurements at a flow velocity of 100 m/s;

the steepness of the leading signal edge correlates with the droplet size.

Chun-Nan Lin, W. Fen-Lu Chang, "Liquid-Droplet Size Measurement with the Hot-Film Anemometer: An Alternative Approach", J. of the Chinese Institute of Engineers, 12, pp. 123–130, 1989:

CTA, conical film, manufactured by TSI;

droplet diameter >500 μm;

a high flow velocity;

an analytical relationship exists with respect to the signal course.

Y. Ozaki, M. Utiyama, T. Fukuyama, M. Nakajima, Y. Hayakawa, "Measurement of droplet size distribution by a hot-film anemometer" in Aerosols, Vol. 1, Proc. Third Int. Aerosol Conf., pp. 663–666, Sep. 24–27, 1990:

CTA, hot-film wire, manufactured by KANOMAX;

water and ethanol droplets;

nearly calm air;

droplet diameter from 1 to 10 μm;

the droplet size can be determined from the electrical energy supplied.

The statement made by Goldschmidt and Householder (1969) that a relationship exists between droplet size and signal maximum is strongly disputed by Bragg and Tevaarwerk (1974); they contend that there is no unambiguous relationship between any signal characterizing variable and the droplet size. However, the studies by Medecki et al (1975, 1979) are in a straight line of development and lead to a commercially available device (see Mahler and Magnus, 1986 and Mahler and Magnus, 1980).

The studies differ from one another most significantly, however, in terms of the probe geometry, probe temperature, flow velocity, droplet type, and evaluation technique. The signal structure ascertained, however, appears to depend strongly on these parameters. Overall, work listed above in the final analysis documents the great panoply parameters in this problem.

For analyzing airborne water droplets in the flow velocity range from 80 to 120 m/s, however, there is no documented measuring method, aside from the above-mentioned preliminary study by Hauf (1983). In determining the droplet size using the hot-film technique, the following basic problems arise:

The precipitation of the airborne droplets onto the hot-film probe is an effect of inertia. Droplets cannot follow the air flow around the probe and strike the probe as a function of their mass and velocity. This size-dependent precipitation (known in English as collection efficiency) can now be calculated for any relevant geometry with the aid of numerical simulation and must be considered to be known. However, this effect occurs primarily in droplets having a diameter below 20 μm.

In the vicinity of the probe, the droplets are braked by the dynamic pressure prevailing there, before they strike the film or some other point of the probe. A droplet is probably deformed on braking, but is surely deformed upon impact. Whether it bursts in the process, or under what circumstances it bursts, is unknown. The fragments of the droplet that adhere to the film, and possibly the entire mass of the droplet, will then flow away from the stagnation point under the influence of the dynamic pressure distribution. During the entire contact time, heat passes into the droplet; the amount of heat transferred is therefore in proportion to the droplet mass that is in thermal contact with the hot film.

Inside the droplet, the heat is distributed by thermal conduction but also by internal circulation. When the boiling temperature is reached, the droplet then evaporates.

It is therefore easy to appreciate the fact that the parameters—probe shape, flow velocity and sensor temperature—affect the behavior of an impacting droplet and its being heated with possible ensuing evaporation.

The typical signal of a single impacting droplet has a very short rise of from 10 to 50 μs, an amplitude of 2 to 3 V, and an approximately exponential decay with a time constant of −2 ms. (These values refer to the CTA hot-film system made by TSI, with water droplets with a diameter of ≈50 μm and a flow velocity of 100 m/s.) Divergent forms have also been found, however, such as maximum amplitudes of 5 to 6 V, a markedly slower rise, rounded maximums rather than sharply defined peaks, a plurality of time constants in the trailing edge, a plateau in the trailing edge, and the like. In wedge-shaped probes, an overswing toward a larger signal has been observed, although this is not a problem of electrical control but can instead be ascribed to a nonhomogeneous distribution of temperature during the impact of the droplets.

In summary, it can be stated that the signal structure thus depends upon the following:

droplet size flow velocity hot-film geometry geometry of the substrate body (wire, cone, disk, etc.)

hot-film temperature material properties of the droplet: density, viscosity, surface tension, specific heat ambient temperature flow direction degree of turbulence droplet repetition rate.

In principle, every parameter exerts some influence on the signal structure, but also affects the action of other parameters, and therefore the influence of the parameters on the signal shape represents a very strongly interlinked, nonlinear problem. The studies done thus far and the publications on them agree, however, in saying that the influence of the flow velocity is high. At low velocities, adhesion of droplets to a hot wire generally occurs, while at high velocity, the contact time of the droplet and the hot film is limited by the flow velocity. Findings cannot therefore readily be adopted to other studies, and in particular the findings of the studies referred to at the outset, done at flow velocities below 10 m/s, cannot be adopted to the range from 50 to 150 m/s.

Another problem in hot-film technology is presented by the signal duration of a single droplet. That is, if a new droplet strikes the hot film before the signal of the previous droplet has faded, then signal superposition occurs. As the impact frequency of the droplets increases, the structure of the individual droplet is lost, while the mean bridge voltage rises. This rise correlates with the total water content of the air, which therefore serves as a measurement principle in many instruments that measure total water content. If individual droplets are studied, a limitation must be made in the number of impacting droplets.

To understand the signal course, as many characterizing variables of the signal as possible must accordingly be detected. Until now, the bridge voltage signal of a bridge circuit was processed in analog fashion, but as a result it was possible to determine only special signal properties, but not the complete set of essential signal properties. Among others, the signal maximums, the amplitudes of the differentiated signal, the length of the plateau, the area below the signal, and the rise and fall times have been studied. However, no analog evaluation methods that determine all of these variables are known. On the contrary, for a predetermined system and with respect to a certain application, only a few evaluation variables have been purposefully studied.

Because of the large number of parameters, all of which influence the signal form of the droplet, and because of the lack of analog analysis methods for completely describing the signal form, until now, only those signal characteristics that are a certain standard for the droplet size could be determined. For certain parameter ranges, particularly at low flow velocities, the signal maximum appears to be a usable standard for the droplet size.

For the parameter range of airborne water droplets at a flow velocity of 50 to 150 m/s, however, there are no studies, other than those by the inventor of the present application, who in a study cited at the outset (Hauf 1983) carried out aircraft-based cloud droplet measurements. In the publication by Lin and Chang (1989), although high velocities are discussed, no values whatever are indicated. In the study by Hauf (1983), it is stated that he furnished the hot-film signal first to a differentiation element and then to a pulse height analyzer. While the differentiation, at droplet repetition rates of a maximum of 20 kHz, does enable determining the rise of the signal, nevertheless the absolute signal height is lost as a measurement variable. If superpositions of a plurality of droplets occur, this goes undetected by the evaluation method.

Since the superposition does not necessarily occur linearly in the rises, as has been confirmed by recent investigations by the inventor, the result is defective determination of droplet size. Moreover, the differentiation of the bridge signal also means that superposed turbulent flying conditions are interpreted as droplets.

Figure 13:
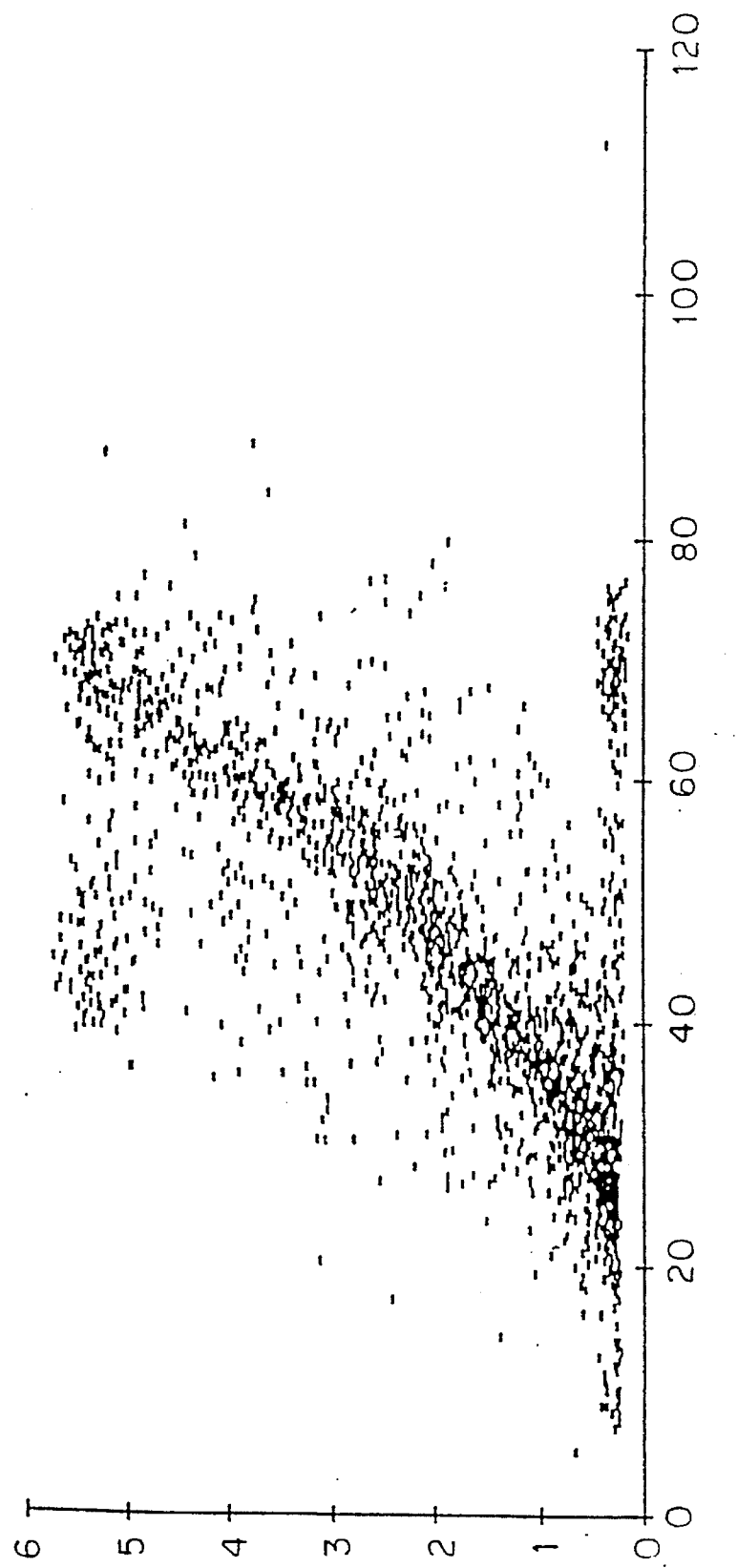

In FIG. 13, a signal maximum is shown as a function of droplet size. The droplets, which had a velocity of 100 m/s, were generated by an ultrasound generator with a vibrating apertured diaphragm with a diameter of 21 µm. The mean diameter was approximately 43 µm. It can be seen from FIG. 13 that although the signal maximum also increases with increasing droplet size, nevertheless considerable scattering occurs at the same time. Precisely at low amplitudes, if signal superposition is present, even large droplets can cause this. This example thus plausibly shows that ignoring important characteristics of the droplet signal, and the lack of systematic studies of the influence of parameters, have not until now led to a promising application of hot-film technology for determining droplet size in the velocity range from 50 to 150 m/s, and in particular plausibly shows why the limitation to the signal amplitude does not yield unambiguous findings.

The object of the invention is to create an economical, robust and maintenance-free method for determining airborne water droplets, which can be used in many kinds of applications, especially in cloud investigation systems carried in aircraft. According to the invention, this is attained, in a method for determining the size of airborne water droplets, by the characteristics of the claim.

According to the invention, the point of departure has been the fundamental concept of determining droplet size with the aid of hot-film technology, which has stood the test of time and is a mature technology. To that end, the signal of individual droplets striking a hot film regulated to constant temperature is used for size determination. To accomplish this, according to the invention not only the layout of the system but also an evaluation method adapted to it, for identifying the droplets and calculating their size from the signal structure, is of definitive significance. It is also assumed that in many cases the user is prepared to make certain sacrifices in accuracy, if the device for determining the droplet size is sufficiently handy and is suitable for being carried on aircraft.

The device according to the invention, hereinafter called a "hot-film droplet system", is also primarily intended for an application to cloud physics. In-situ investigations in clouds are done in the aircraft whose measured speed is typically in the range from 50 to 150 m/s. This is also the reason for the major interest in this velocity range. In the measuring method of the invention, it does not matter whether the probe moves with the aircraft through the cloud, or is mounted stationary and exposed to a flow of water droplets. Thus the hot-film droplet system of the invention can be used not only in clouds but also in technical fields.

In the hot-film droplet system according to the invention, the hot-film technique is supplied to airborne water droplets in the velocity range from 50 to 150 m/s, particularly since it has learned in the meantime that the flow velocity has a decisive influence on the signal structure. Moreover, the hot-film droplet system according to the invention is distinguished over the known methods, processes and equipment in the following ways: At a maximum regulating frequency of approximately 450 kHz of a commercially available hot-film device, the rise times of a droplet signal are at minimum 10 µs. If the electronic calibration of the circuit is unsatisfactory, the maximum regulating frequency can drop still further, since a droplet with a diameter of 100 µm at a flow velocity of 100 m/s requires a minimum time of 1 µs to move from the instant of first impact to full thermal contact; a sampling rate of approximately 1 MHz is thus required for comprehensive signal analysis.

Fluctuations in temperature, wind and density in the air moved past the sensor cause time-dependent fluctuations in the heat transfer from the sensor to the environment and thus fluctuations in the bridge voltage. This involves two problems:

a) The signal of an impacting droplet must first be recovered from its background fluctuations, because these fluctuations limit the detectability of small droplets; the lower limit itself is not a fixed variable but is in the range of diameters of $\geq 1$ µm. With the aid of an identification algorithm according to the invention, a droplet is detected, on the basis of the squared bridge signal ($U^2$), if the signal height—measured from the base point—has exceeded a certain command value.

b) Since the pure droplet signal has undesired effects superimposed on it, such as e.g. caused by turbulent flow fluctuations, and must be cleansed of them, an essential characteristic of this interfered-with droplet signal is the absence of monotony, or in other words the occurrence of a plurality of relative maximums. This makes droplet identification considerably more difficult. With the identification algorithm of the invention, the problem can be solved in a plurality of parallel running processes, which will now be listed:

In the first process, a digital three-point filter is used to eliminate bit discontinuities, and the input signal is then squared.

In the second process, the signal is broken down into an elementary signal of the following form:

$$\text{minimum} < \text{maximum} \geq \text{minimum}.$$

In the third process, two elementary signals are compared; if negligible fluctuations ark identified, they are then put together and a threshold value is looked for droplet recognition, or the resultant values are discarded.

In a fourth process, the signal characteristics, such as maximums, area, rise time, and so forth, are determined.

In the fifth process, the signal characteristics in the event of superposition are corrected, and the droplet size is determined, and corresponding data are output.

The evaluation logic of this parallel method processes is complex.

The information flows hierarchically from top to bottom. With each additional process, the data rate drops while there is a simultaneous increase in processing time per data set, so that the calculation time for each process is approximately the same.

From extensive tests and in view of indications in the literature, it has been found that from the set of signal identifying variables, the area below the squared voltage signal is the best standard for droplet size. This evaluation variable is the direct result of the hot-film measuring principle. The impacting droplets in fact draw heat from the hot film, which is tracked in the form of electrical energy. The latter is proportional to the time integral over the squared bridge signal; that is, $\int U^2 dt$; it can therefore be determined from the signal course. In the identification algorithm, the squared bridge signal ($U^2$) is analyzed. The electrical energy supplied is thus a standard for the droplet size.

The dwell time of a droplet on the hot film is velocity-dependent, and hence corrections must be made. The droplet identification algorithm, with the aid of the energy balance of the droplet, enables measuring the signal area exactly, even in the case of superposition droplets and if the background signal fluctuates severely.

The findings of the tests done are that the influence of the parameters of sensor geometry, flow velocity, film temperature, form of the substrate body, droplet frequency surface tension, and the sensor readout has been optimized. Nevertheless, the droplet identification algorithm must be adapted to the particular parameter values. The signal course at a low film temperature, for instance, is flatter and rounder than at a high temperature. In a plurality of iterative steps, a panoply of parameters can be narrowed down. By less streamlined design of the probe body in which the hot film is integrated flush, the impact likelihood of small droplets (with a diameter <20 µm) can be reduced in a targeted way. The point of departure for this is the impact likelihood, which is calculatable numerically for predetermined geometries and droplet spectra, as a function of the droplet size. In accordance with the invention, it is therefore possible to blank out small droplets, or in other words to lower the so-called size-dependent deflection (collection efficiency) by suitable shaping of the probe body. This blanking out of small droplets might be desirable, e.g. in natural clouds, as the droplet identification algorithm is limited to a maximum number of drop hits of ≈500 per s. This is further described below.

The hot-film droplet system according to the invention is thus distinguished from earlier methods and equipment known to the inventor by its application to the velocity range from 50 to 150 ms/s, by digital detection of the droplet signal, by a droplet identification algorithm adapted to the signal structure, by a complete determination of the signal characteristics, by an optimal design of the hot-film probe, and optionally by a selecting blanking out of droplets having a diameter below 20 µm.

Figure 3:
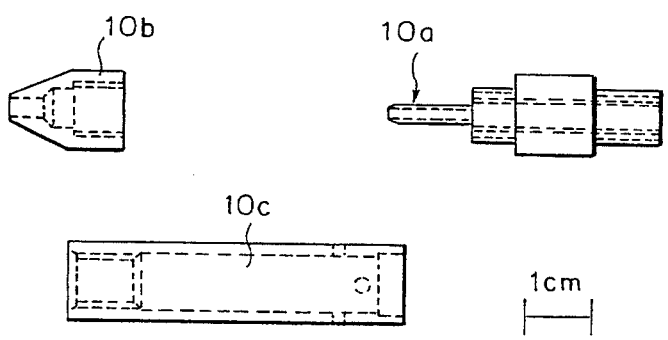
Figure 2:
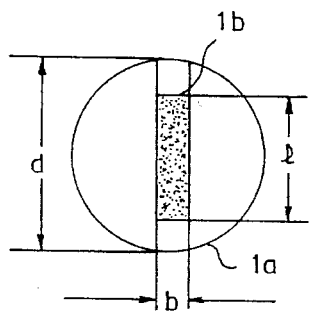
Figure 4:
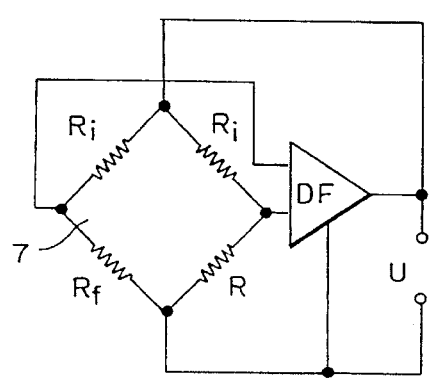
Figure 5:
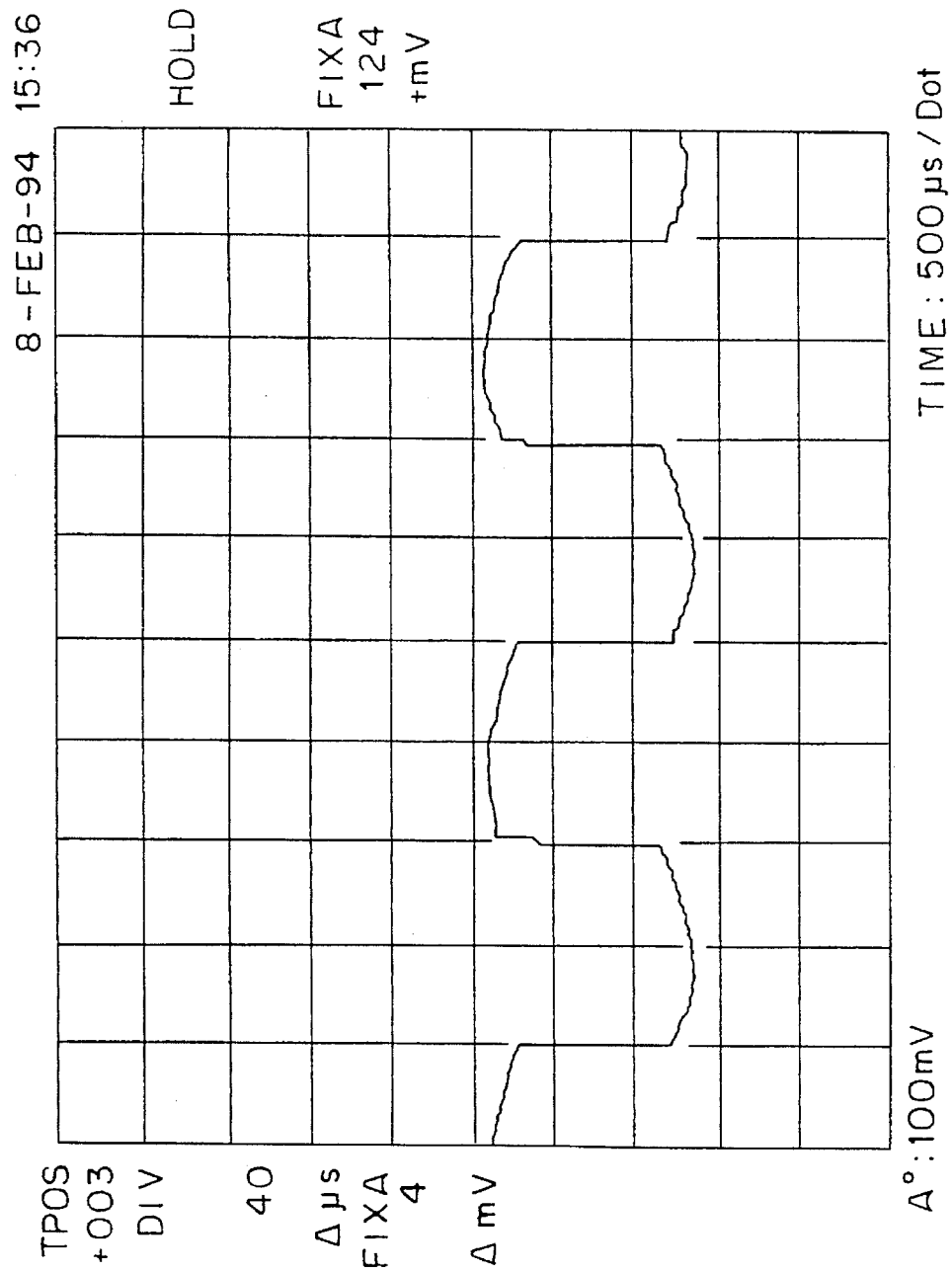
Figure 6:
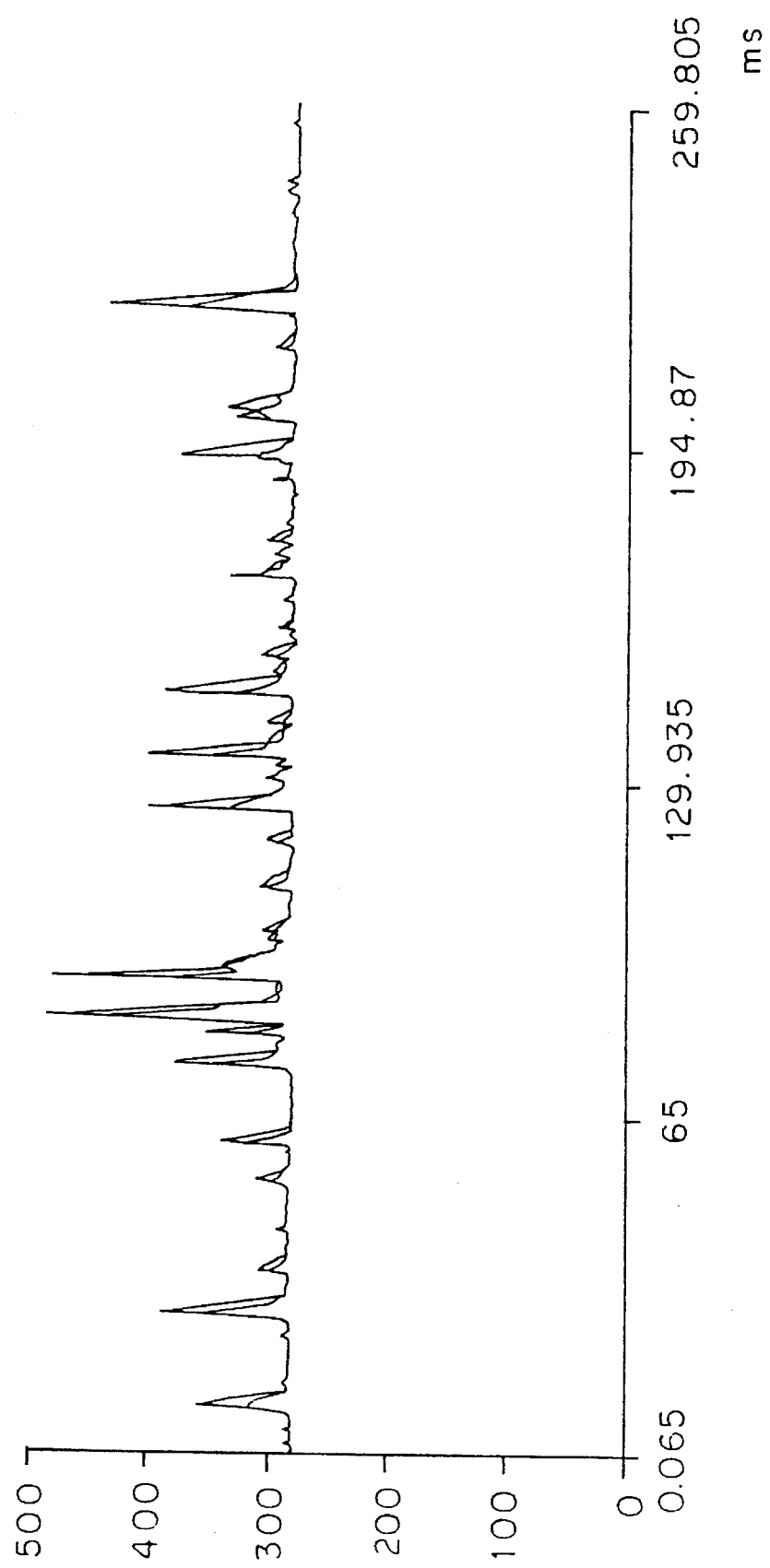
Figure 7:
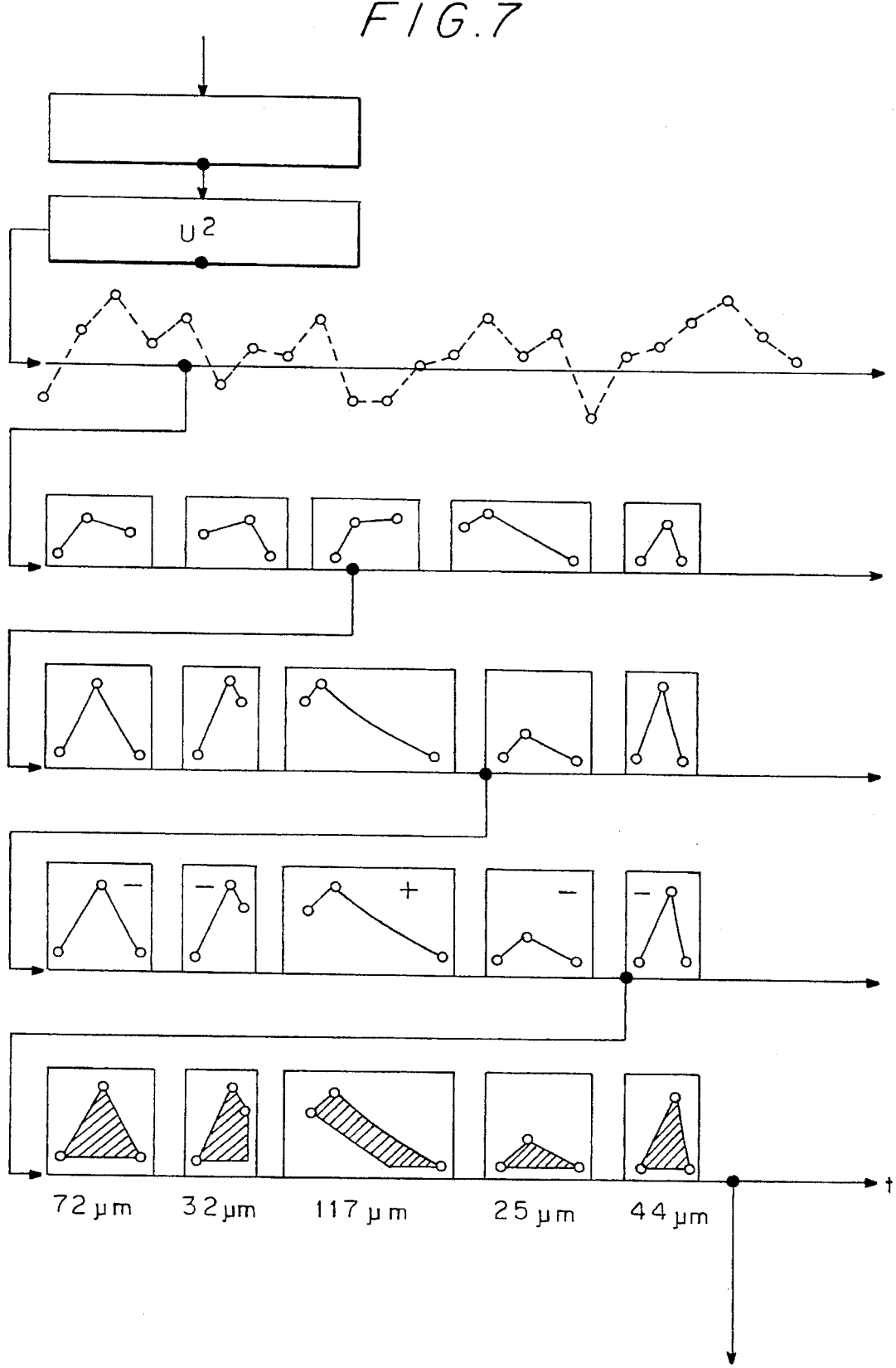
Figure 8:
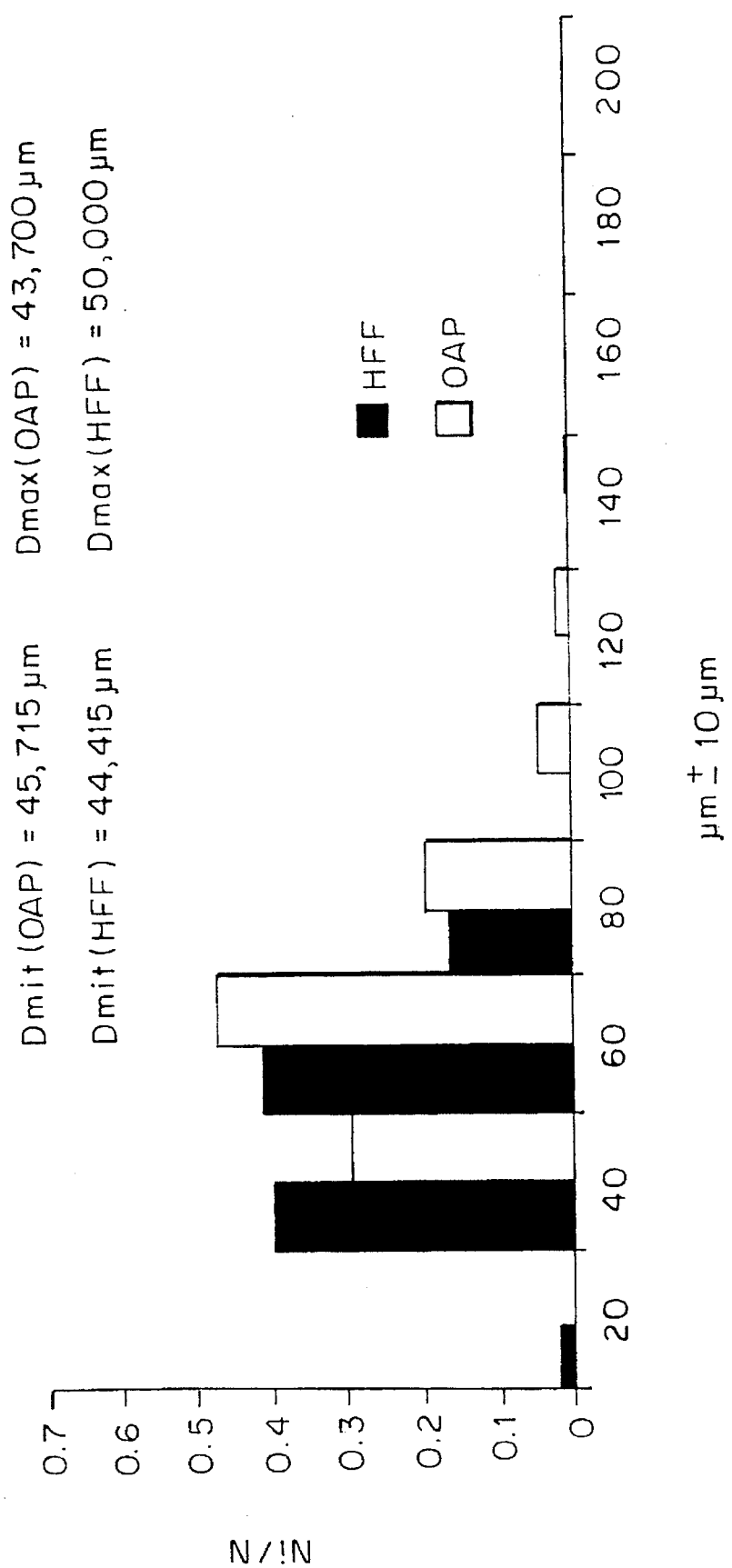

The invention is described in detail below in terms of preferred embodiments, in conjunction with the accompanying drawings. Shown are:

FIG. 1, in the form of a schematic basic illustration, the layout of an embodiment according to the invention of a device for determining droplet size;

FIG. 2, an illustration, not to scale, of a face end of a flat hot-film probe;

FIG. 3, a schematic illustration of a probe body shown in the form of individual parts;

FIG. 4, a schematic illustration of a CTA bridge circuit;

FIG. 5, a computer expression that illustrates a bridge calibration;

FIG. 6, a diagram on whose abscissa the digitized time series of a bridge voltage and on whose ordinate the associated signal amplitude of detected droplets are plotted;

FIG. 7, a fundamental structure of an evaluation program, in which various stages in the signal processing are shown;

FIG. 8, a diagram of a comparison of measured droplet spectra;

FIGS. 9–12B, diagrams of comparisons of various droplet spectra; and

FIG. 13, a diagram with a signal amplitude, plotted on the ordinate, as a function of the droplet size, in the form of a droplet diameter, plotted on the abscissa.

The hot-film droplet system according to the invention is a measuring method for continuously determining the size of airborne water droplets that have a diameter of 1 to 100 µm, and a weight of between $0.005 \cdot 10^{-12}$ kg and $500 \cdot 10^{-12}$ kg, in which the hot-film technique is employed at a flow velocity of 50 to 150 m/s.

As schematically shown in FIG. 1, the hot-film droplet system is provided with a hot-film probe 1, which has a probe body shown in FIG. 3 and a hot film, a hot-film operating device in the form of a CTA measurement bridge 2, a data detection unit 3 with an analog/digital converter, a data evaluation unit 4 with a computer and signal processing, and a data output unit 5 and a memory 6.

As can be seen from FIG. 1, the hot-film probe 1 is connected via a cable, not identified by reference numeral to the hot-film operating device and the CTA measurement bridge 2. The data detection unit 3, the data evaluation unit 4, the data output unit 5 and the data memory 6 are combined in a personal computer, so that this computer carries out the data detection, data output, data storage and data evaluation. The CTA measurement bridge 2 and the PC, not shown, can also readily be accommodated in the same manner.

FIG. 2 shows the face of a flat hot-film probe. An active, heated hot film 1b has a platinum film with a thickness of 0.5 µm, which is vapor-deposited from quartz onto a substrate body 1a. In so-called flat probes made by TSI, model 1471, the active hot film 1b is a strip of width b of 0.22 mm and a length l of 0.93 mm; the hot film 1b is vapor-deposited onto a disklike substrate glass 1a that has a diameter d of 1.5 mm, which is not shown to scale in FIG. 2. Electrical power is supplied from the side, but this is not shown in detail in FIG. 2. The active measurement area $F=b \cdot 1$ is thus 0.205 mm², while the area of the substrate body is 1.79 mm². Since the exact dimensions vary from one probe or sensor to another, they must be redetermined each time by means of a microscope.

Care must be taken that the number of droplets impacting per unit of time is proportional to the film area F. That is, if the area F is chosen to be too large, the droplet repetition rate rises and can cause signal superpositions, so that individual droplets can no longer be resolved with the same quality. With the area of the platinum film 1b, its resistance $R_0$ at a predetermined temperature varies as well. Therefore the manufacturing company TSI also indicates the temperature coefficient $T_k$; typical values by way of example are a resistance $R_0$ of 4.71 Ω and a temperature coefficient $T_k$ of 0.97 Ω/100° C.

The probe body itself is in three parts, as can be seen in FIG. 3. A quartz glass disk 1a (see FIG. 2) with a hot film 1b is secured to the front end of a substrate bar 10a made of PVC. A conical protector 10b, likewise of PVC, is screwed to the substrate bar 10a. This protector that can be screwed on is available, unlike the conical form shown in FIG. 3, as a cylinder as well (in the case of a cylinder, the hot film is integrated flush with the face end of the cylinder). In a cone, the influence of the hot-film probe on the flow field surrounding it is less than in the case of the cylinder.

The parts that can be screwed on, such as the conical protector 10b, can therefore also be utilized to purposefully vary the likelihood of droplet impact. (Relatively large cylinder diameters mean that smaller and smaller droplets will strike the face end and thus the film, since the flow field is interfered with more and more as the diameter increases.) This can be significant if—as in clouds—a very great number of small droplets strike the probe, and the droplet identification algorithm longer "sees" any individual droplets, since the droplet signals are continually superimposed on one another. For that reason, the interfering body size and the film area must be adapted to one another, although with a commercially acquired probe only the inferfering body size can then be varied.

The two probe parts 10a and 10b of PVC are secured to a probe holder 10c of stainless steel. Accommodated in its housing, along with two supply lines, not shown in detail, to the hot film, likewise not shown, is also a reference resistor $R_f$ (not shown), by means of which the resistance of the hot-film resistor R and hence the hot-film temperature $T_f$ are defined. The reference resistor $R_f$ of a bridge circuit (see FIG. 4) is therefore, as in a classical four-lead circuit, located in the immediate vicinity of the hot film 1b, and is therefore exposed to the same external temperature fluctuations.

The maximum allowable hot-film temperature is set by the manufacturer; for a particular probe with a resistance of 5 Ω, for instance, it is 120° C. In order that the signal height with be correspondingly large, the highest possible film temperature is desirable. The signal-to-noise ratio thus rises as well, which makes the droplets more easily detectable. With increasing film temperature, the influence of a fluctuating ambient temperature on the film variable (see equation (6) given below) drops as well. The probe holder 10c is provided with a plug—not shown in detail—and can then be plugged to a second holder, likewise not shown, for instance being secured to an aircraft.

As already noted at the outset, hot-film or hot-wire systems can be operated either by a constant current method (CCA) or a constant temperature method (CTA). The hot-film droplet system according to the invention is operated by the CTA method, since the fact that the film temperature is kept constant is favorable for calculating the heat transfer from the film to the droplet (see equation (6) given below). For this reason, the IFA-100 CTA made by TSI was used.

The geometric CTA bridge circuit schematically shown in FIG. 4 is also used; it has "upper" resistors $R_i$ of 20 Ω, the reference resistor $R_f$, and the hot-film resistor R whose resistance is to be measured. This type of bridge circuit has a low noise level and high frequency response of up to 450 kHz. The supplied bridge current was 0.3 A. Since the CTA measurement bridge circuit in FIG. 4, as a feedback system, is capable of vibration, the bridge circuit including the hot film 1b, the reference resistor $R_f$, and cables must be correspondingly calibrated in order to suppress and prevent such undesired oscillation in the measurement signal.

FIG. 5 shows a bridge calibration, plotted by the output unit of the computer, which is the response of the measurement bridge circuit (FIG. 4) to a rectangular signal fed to it. As can be seen from FIG. 5, the signal structure is reproduced well, and in particular no overswings occur at the edges.

As can be seen from FIG. 6, recordings of the output voltage of the CTA measurement bridge circuit (FIG. 4) have fluctuations in the range of a few microseconds, particularly in the droplet signal. To resolve these fluctuations, and especially to be able to calculate the area under the droplet signal exactly, a sampling frequency of 1 MHz is necessary. However, the maximum sampling frequency is dependent on the number and size of the droplets and also on the flow state and can possible, in order to reduce the incident amount of data, can also be lowered to values of 250 kHz. For analog/digital conversion and ensuing data evaluation, a PC plug-in card of the kind known as SCOPE made by IMTEC has been used; this can also be integrated into a PC.

In FIG. 6, a digital time series of the bridge voltage has been plotted on the abscissa, with the time entered in milliseconds (ms). On the ordinate, the signal amplitude measured at the hot-film sensor resistor R of the bridge circuit (FIG. 4) is plotted in digits. In the diagram of FIG. 6, droplets detected are represented by straight connecting lines from the base point through a signal maximum to the terminal point. The mean voltage level between two droplets is represented by a straight line. In the diagram shown in FIG. 6, the flow velocity was 100 m/s, and the most frequently encountered mean diameter of the droplets was 30 μm. The droplets were produced by an injection needle that had an inside diameter of 0.6 mm.

For data evaluation, an evaluation program and a computer in the form of a personal computer (PC), in which this program is implemented, were used. Since the data, at a rate of 1 MHz, could not be acquired continuously and simultaneously evaluated, measurement and evaluation were done in alternation. The ratio between measurement time and evaluation time for the PC used was 1:40. However, this value depends among other factors on the clock speed of the processor, which was 33 MHz. The program used for evaluation, with a total of 1500 Turbo Pascal lines, can easily be implemented with one or two signal processors (DSPs). However, the program structure is designed such that in principle, parallel processing on a plurality of processors is also possible, so that continuous real-time acquisition and evaluation can be done.

According to the invention, the determination of droplet size is based on the hypothesis that the quantity of heat given up by the hot film to a droplet serves a) to heat the droplet from the ambient temperature $T_E$ to the applicable boiling temperature $T_s$, and b) then to evaporate it completely.

The electrical energy given up to the droplet is $$\Delta E = \frac{R_f}{(R_i + R_f)^2} \int_0^{t_c} (U^2 - U_0^2)dt \qquad (1)$$

where $R_f$ is the reference resistor, $R_i$ is the "upper" bridge resistor at 20 Ω, U is the bridge voltage, $U_0$ is the bridge voltage without droplets, and $t_c$ is the characteristic droplet signal time.

The amount of heat supplied to the droplet is $$\Delta Q_H = Mc_w(T_s - T_E) \qquad (2)$$

where N is the droplet mass, $c_w$ is the specific heat of water, $T_s$ is the boiling temperature of water at ambient pressure, and $T_E$ is the ambient temperature. $\Delta Q_H$ is the quantity of heat that is used to raise a droplet from the ambient temperature $T_E$ to the boiling temperature $T_s$.

The quantity of heat $\Delta Q_V$ required for evaporation at boiling temperature is $$\Delta Q_V = ML_v(T_s) \tag{3}$$

where $L_v(T)$ designates the heat of evaporation of water at the temperature T.

From the energy balance, $$\Delta E = \Delta Q_H + \Delta Q_V \tag{4}$$

and assuming spherical droplets, where $$M = \frac{4}{3} \pi \rho_w (d/2)^3 \tag{5}$$

the following is found for the droplet diameter d:

$$d^3 = \frac{6R_f \int_0^{t_c} (U^2 - U_0^2) dt}{\pi \rho_w (R_i + R_f)^2 [c_w(T_s - T_E) + L_v(T_s)]} \tag{6}$$

The hypothesis of the energy balance at the hot film thus enables a determination of droplet size without requiring calibration factors. The measurement variable here is the integral over the electrical power additionally supplied during the contact time $t_c$. The integral is determined by means of the evaluation algorithm. Equation (6) also shows that the primary measurement variable is the droplet mass $M \sim d^3$. Calculating the droplet size d from equation (6) means no more than a change of scale, in terms of the mass scale.

The measuring method of the invention is limited by several factors. These are:

The minimum droplet size, limited by the smallest practically predeterminable threshold value of the droplet identification algorithm.

If the amplitude threshold value, which is 3 $V^2$, which is approximately 3% of the total dynamic range, is chosen to be too small, then incidental fluctuations will be detected as droplets; conversely, if it is chosen to be too large, then small droplets will unnecessarily be discarded.

Frequency response of the bridge circuit

A limit frequency of 450 kHz is given by the manufacturer for the hot-film probe used. Since the signal rise time and thus the time until maximum heat transfer is limited by the frequency response, the shortest droplet rise times observed, of a few milliseconds, do not enable learning whether the frequency response of the CTA measurement bridge circuit limits this rise time and whether the process of impact and heating up of the droplet would actually be faster, or whether the processes in fact are so slow and the measurement bridge circuit is faithfully reproducing the rise time. Thus the frequency response, if anything, adulterates not the quantity of head calculated but rather the signal characteristic.

Maximum amplification of the bridge circuit

The bridge circuit is limited to 13 V. If no droplets strike the probe, then the mean voltage level, as a function of the flow velocity, is 6 to 7 V, and so the useful signal is also approximately 6 to 7 V. A higher voltage and hence higher power are not possible, because that in the final analysis would merely adulterate the signal characteristic.

Signal duration or time for heating up of the droplet

Typically, a time of approximately 2 ms is needed for the droplet with a diameter of ≈40 μm. In a predetermined period of time of one second, for instance, approximately N=500 droplets can therefore be determined. If more droplets impact, then the droplet repetition rate is increased as well; the result is superposition of the signals, which in principle is analyzable as long as not too many droplets impact, and the signal can fade again at some time.

The droplet repetition rate is determined by the following:

1. The existing droplet spectrum; in natural clouds, there are generally far more small droplets (less than 10 μm) than in technical fields;
2. The sensor area; the greater the area, the higher the droplet repetition rate;
3. The sensor temperature; the greater the sensor temperature, the shorter are the fade time and thus the signal length;
4. The flow velocity; the greater the flow velocity, the higher the droplet repetition rate; and
5. The sensor shape. The impact likelihood and hence the droplet repetition rate are thus determined by the sensor shape.

The minimum time for a droplet to heat up dictates a maximum droplet frequency, which is at approximately 500 Hz. One possible way to keep the droplet repetition rate below this maximum value resides in the shaping of the probe body. As said above, with increasing cylinder diameters the collection efficiency (or impact likelihood) of small droplets with diameters less 20 μm is lowered.

The resolution of the A/D converter at 1 MHz

The fundamental structure of an evaluation method is shown in FIG. 7. As can be seen from FIG. 7, information is hierarchically passed from one stage to another, specifically from top to bottom. An information flow in the opposite direction does not take place. The data flow structure shown is also highly suitable for parallel processing; at maximum, the same number of processors as there are stages should be used. Naturally, the evaluation program can also be processed sequentially in which case the stages are replaced with loops. Only the basic structure will be described below, and program details will be dispensed with.

The digitized voltage values are subjected to a three-point filter, which essentially eliminates bit discontinuities. The squared voltage values are then further processed (See the line, marked "(Voltage)$^2$", below the block marked "$U^2$".)

The signal is broken down into a sequence of elementary signals of the following form:

minimum<maximum≧minimum

This breakdown of an arbitrary time series is unambiguous and continuous. For every elementary signal, a complete set of identifying variables is calculated. These include: base point, rise time, maximum, fall time, terminal point, area below the leading edge and below the trailing edge (see the line designated "elementary signal").

Next, two adjacent elementary signals are compared with one another. Distinctions are now made between cases. If the signal rise is greater than a predetermined, empirically determined threshold value, then the elementary signal is recognized as part of a droplet signal. If the minimum between the elementary signals is less than a predetermined, empirical value, this relative minimum is recognized as a fluctuation that is not relevant for droplet signal determination. This case typically occurs in the rising or leading-edge portion of the droplet signal. In the trailing portion of the droplet signal, a relative maximum is similarly recognized to be irrelevant.

In both cases, the two elementary signals are combined into one. However, if neither the elementary signals are combined nor a droplet is identified, then the first elementary signal is discarded. The comparison is then repeated with the second and third elementary signals, and so forth.

However, if an elementary signal has been detected as a droplet, then it is compared with the droplet determined before that, and a check is made as to whether a superposition effect is involved. Such an effect is present if both identified droplets immediately succeed one another. In this way, droplets and superposition signals are distinguished from one another.

The droplet size is determined in accordance with equation (6). Corrections are also made for the accurate area calculation in the event of a signal superposition. All the identifying variables of a droplet are output.

In FIG. 6, the original time series of the original bridge voltage and the droplets recognized by the evaluation program are shown in the form of straight connecting lines extending from the base point through the maximum to the terminal point. FIG. 6 also shows that the algorithm detects virtually all the droplets, including the superposition droplets.

Next, the data vector with the droplet information is stored in a medium suitable for that purpose, such as tape, a removable disk, and the like. The size distribution function can be calculated on line via predetermined time intervals and output as needed. Other statistical variables, such as droplet rate, mean value, or maximum or width of the droplet distribution, can likewise be calculated on line and shown in graph form or stored in memory. FIG. 8 as a typical measurement example shows the droplet size distribution that is determined with the hot-film droplet system according to the invention and compared with an optical imaging system OAP made by PMS. The droplets were produced here with an ultrasound sensor with a vibrating apertured diaphragm with a diameter of 21 μm. The flow velocity was 100 m/s. According to manufacturer specifications, the droplets on average should be twice as large as the apertured diaphragm; this means they would have a diameter of 43 μm. The hot-film droplet system, in accordance with equation (6), for a mean value of 44 μm and for the maximum value of the distribution, produces a diameter of 50 μm. In comparison, the optical reference method furnishes a mean value of 46 μm and a maximum value at 44 μm. From this measurement example it can be seen that the hot-film droplet system according to the invention agrees quite well with the value to be expected both from the optical method and the so-called generation principle.

Further exemplary embodiments will now be described. In order to carry out tests in the velocity range from 80 to 120 m/s in a free-jet wind tunnel, the wind tunnel was operated with compressed air, and if it is equipped with a nozzle with a diameter of 3.81 mm, it attains a maximum flow velocity of 150 m/s. The probe is then positioned in the middle of the jet, and the area F of its active platinum film 1*b* was 0.205 mm$^2$.

Water droplets were then introduced into the jet and strike the film. For droplet generation, an ultrasound atomizer, an ultrasound generator with a vibrating apertured diaphragm, a needle atomizer with an inside diameter of 0.6 mm, and a needle atomizer with an inside diameter of 0.2 mm were used.

First, series of measurements with the hot-film droplet system according to the invention were recorded. The tests were then repeated with optical measuring instruments instead of the hot-film device. The optical measuring instruments are sold by PMS and, as already noted above, represent the most widely used measuring instruments for determining droplet size.

Figure 9:
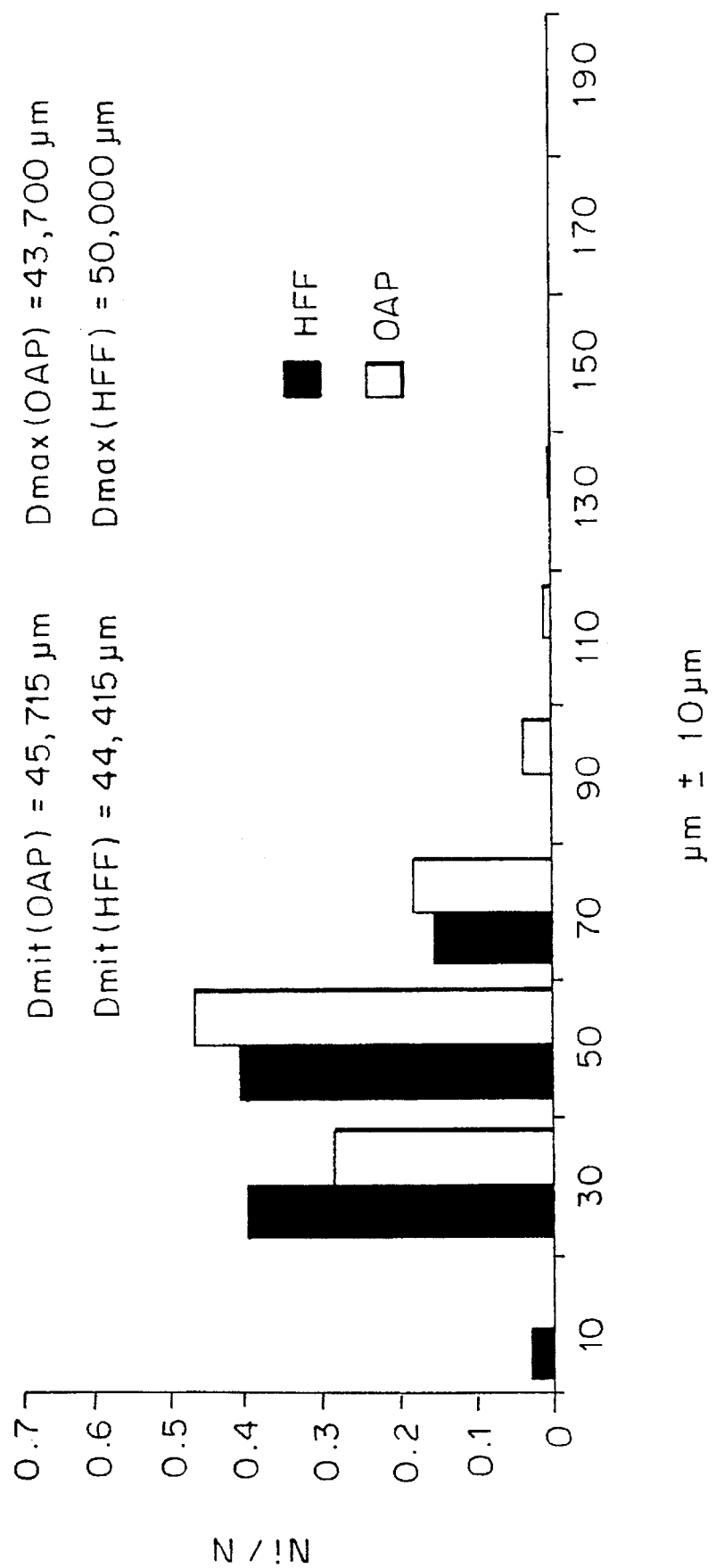
Figure 10:
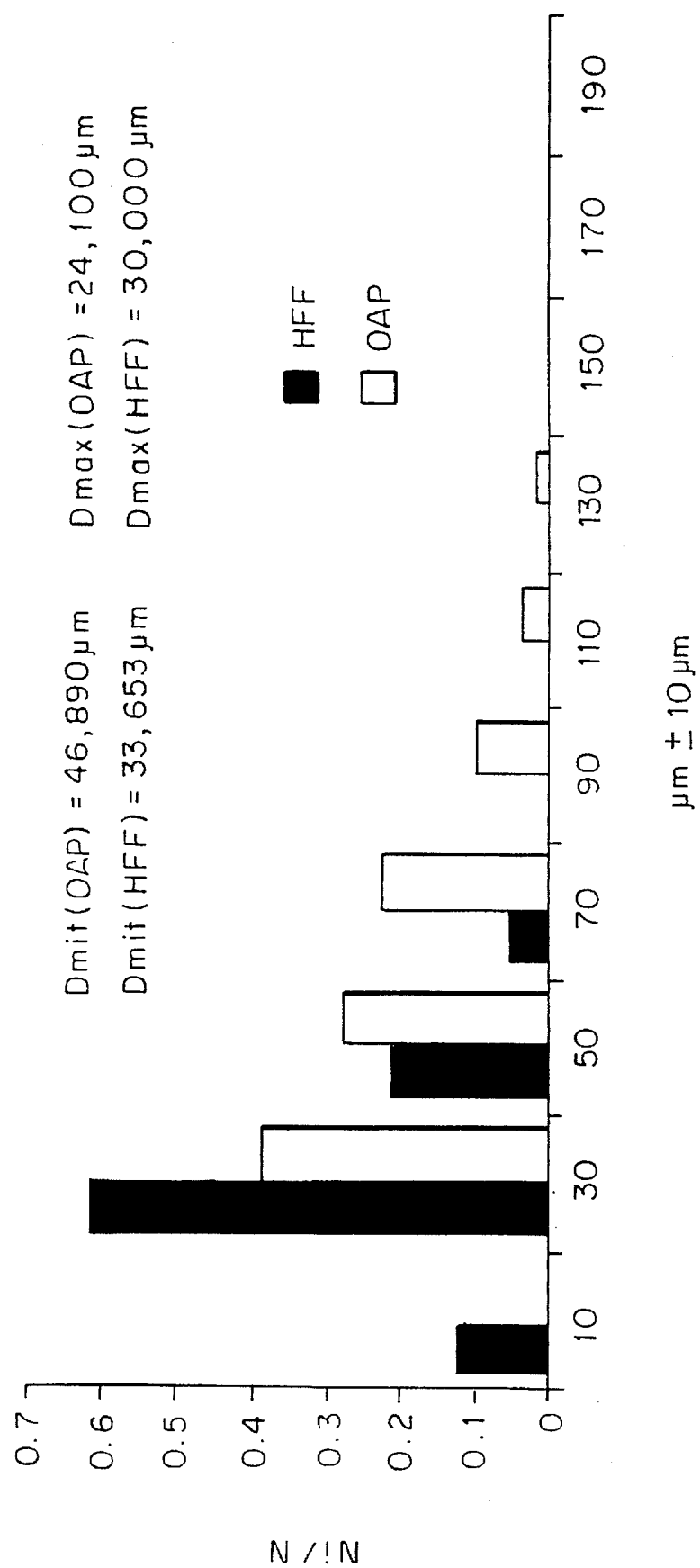
Figure 11:
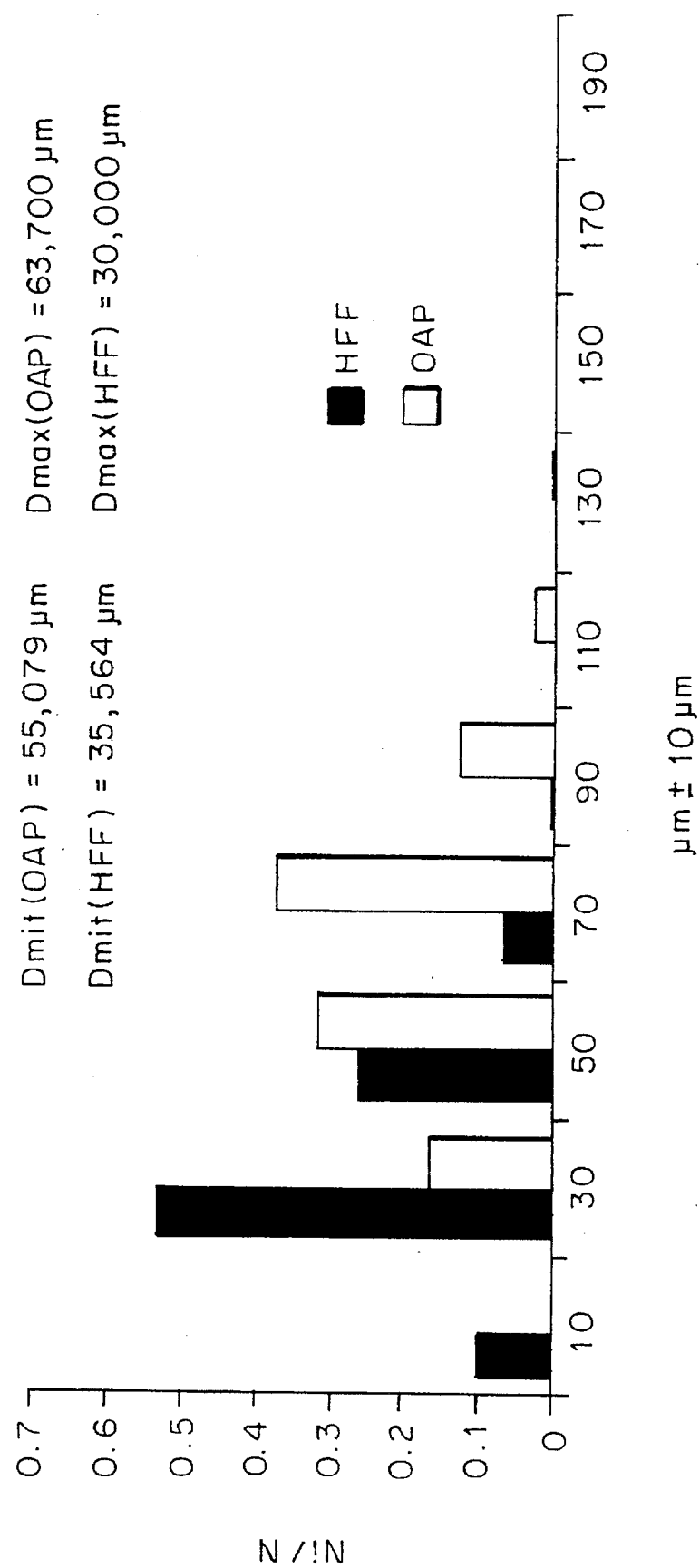

One of these optical measuring instruments, an FSSP (forward scattering system probe) sensor, measures the forward scattering of a laser beam for droplets with a diameter from 0.5 to 47 μm. The OAP (optical array probe) sensor produces a shadow, which is measured with the aid of a diode array, and is usable for droplets with a diameter from 20 to 600 μm. In FIGS. 8–10, the various coherent distributions of droplet size are shown. All the distributions were evaluated by the same method, which has been described above in great detail.

Numbers of droplets measured in the various size classes are standardized with the total number and are shown as a function of droplet size. The vertical axis shows the proportion of measured droplets in each size class, that is, the number of droplets ($N_i$) divided by the total number of droplets ($N$). In evaluating the comparison, it must be remembered that the generation of small droplets, their acceleration to a flow velocity of 100 m/s without a size change, and the determination of droplet sizes all involve certain difficulties, which is why, within a certain size range, differences of more than 100% in the number of droplets are not unusual.

In FIG. 9, droplets were produced with an ultrasound generator or atomizer with a vibrating apertured diaphragm having a diameter of 21 μm, and a droplet spectrum with a maximum at 43 μm was thus generated. The two devices that are compared with one another, namely the OAP sensor and the hot-film sensor, furnished virtually exactly the same mean value of approximately 44 μm. The size distribution can also be said to agree (since the OAP sensor has a lower measuring range limit of 20 μm, the standardized size distribution shifts toward larger droplets).

A similar result to that given in FIG. 9 is the droplet spectrum produced by an injection needle in FIG. 10. Here the injection needle had an inside diameter of 0.6 mm, and the flow velocity was 100 m/s. The maximum value of the droplet spectrum in the two systems was within a size interval of 20 μm and 40 μm, respectively. Once again, in the OAP sensor small droplets are left out, while the hot-film droplet system is unable to resolve droplets that have a diameter larger than 100 μm.

If the proportion of droplets with a diameter of over 100 μm in a spectrum increases, for instance if an injection needle with another diameter is used, such as 0.2 mm (see FIG. 11), then these differences become quite clear. However, both the mean value and the maximum of the droplet spectrum still agree relatively well. In view of the measurement problems, differences of from 5 to 10 μm can be considered negligible.

Figure 12A:
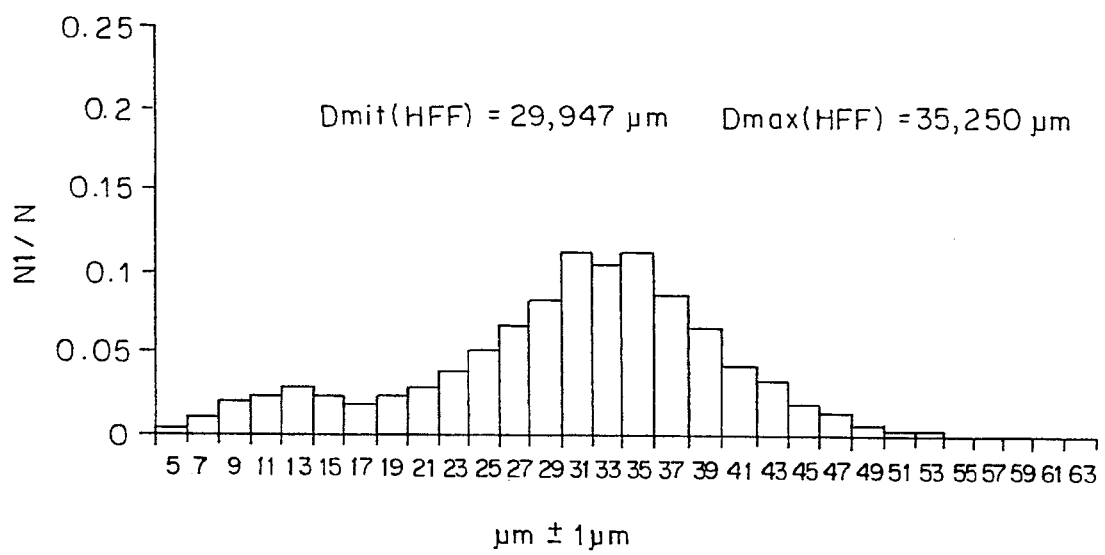
Figure 12B:
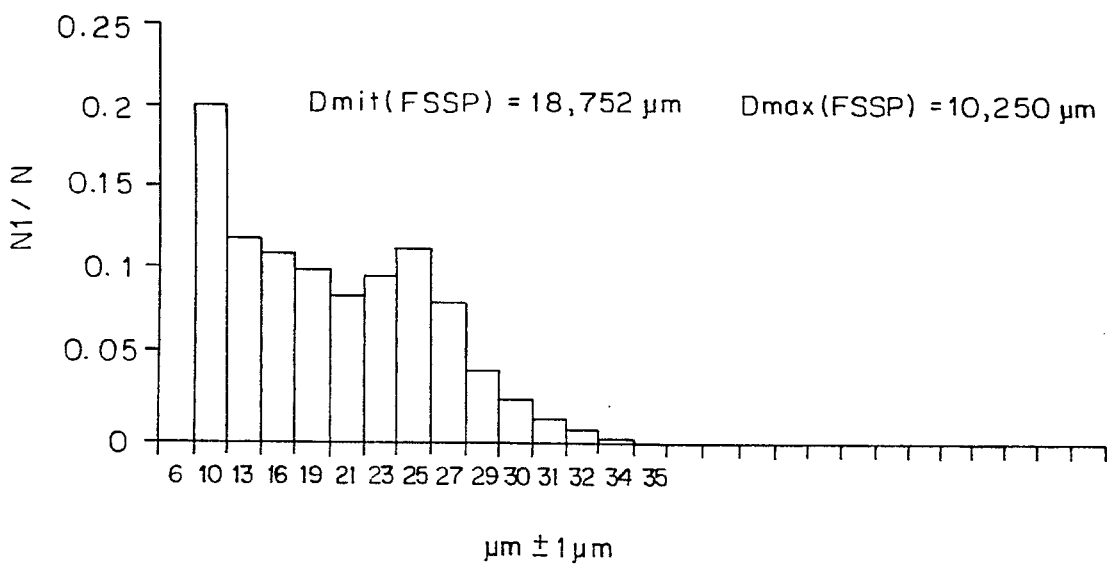

In the last measurement example, shown in FIGS. 12A–12B, an ultrasound atomizer generated a droplet wave, which is drawn into the free jet by a negative pressure, as a result of which the droplet spectrum must be expected to have changed. According to the specifications of the manufacturer, the centroid of distribution should be at approximately 15 μm. This can be reproduced quite well by the FSSP sensor. A second peak in the spectrum at 25 μm can also be seen in FIG. 13. (See FIG. 12B.) However, the hot-film droplet system according to the invention evaluates this sensor point more strongly than the first peak, which is at 13 μm, but nevertheless is clearly visible. Both measurement systems reproduce the bimodality of the droplet spectrum, with peaks at 10 to 13 μm and at 25 to 33 μm, quite well. The reason for the bimodality should with great certainty be the coagulation of smaller droplets upon acceleration in the free jet. The measurement findings obtained are readily interpreted and can also be explained in the context of the possible, known sources of error.

The hot-film droplet system according to the invention furnishes size measurements of airborne droplets that have no obvious errors and that appear to be of equal value to those of the far more complex optical methods.

As may be learned from the above description, the comparison measurements carried out with the hot-film droplet system according to the invention agree quite well. Differences in the mean and maximum value of distribution are smaller than 10 μm. Thus they are also smaller than the error in the optical method and in any other method used thus far for determining the size of airborne water droplets of this size range and at this flow velocity. Tests carried out have confirmed its applicability in the range from 50 to 150 m/s.

With the hot-film droplet system of the invention it is thus possible continuously to determine the size of airborne water droplets, having a diameter from 10 to 100 μm in the velocity range of from 50 to 150 m/s, with adequate accuracy.

The number of water droplets striking the measurement probe may be purposefully varied, by means of a suitable hydrodynamic shaping of the measurement probe body (10a–10c), such that the number of small droplets with a diameter below 20 μm is reduced to a number that is still detectable by the method. That is, to reduce the frequency of droplet impacts to a frequency that the processor and program can handle, droplets smaller than about 20 μm can be deflected away.

The computer program may be adapted to the special structure of the probe, and the program is then dependent on the probe geometry, flow velocity, film temperature, droplet rate and surface tension, of the voltage output signal of the bridge circuit.

Conversely, the program may be corrected for variables of flow temperature, flow velocity and heat dissipation at the probe body.

What I claim is:

1. A method for determining the size of airborne water droplets having a diameter in the range from 1 to 100 μm and a velocity of from 50 to 150 m/s relative to a measurement probe, using the measurement probe, an operating device with an integrated A/D converter, and a signal processor; the method comprising the following steps:

(a) providing a flat platinum film approximately 0.5 μm thick, vapor-deposited onto a quartz disk and orienting a film-bearing face of the disk to an oncoming water-droplet-bearing air flow axially perpendicular to the film-bearing face, the disk being integrated into a probe body of the measurement probe on a flow-facing front face of the probe body oriented toward impacting water droplets of the flow, the film having an area smaller than 1 mm$^2$;

keeping a temperature of the film constant at a temperature above 100° C. by means of a bridge circuit in the operating device with a regulating frequency of more than 200 kHz;

(b) digitizing an analog voltage output signal of the bridge circuit over predetermined measuring time intervals by means of the A/D converter at a selected frequency from 0.1 to 1 MHz and further processing the digitized output signal of the bridge circuit by means of a computer program of the signal processor, which program:

(i) recognizes a signal of an individual impacting droplet and distinguishes the signal of the droplet from signal fluctuations caused by air-flow velocity fluctuations;

(ii) also identifies the signal of a droplet, even if the signal of the droplet that impacted previously has not yet decayed to a baseline value; and (iii) for each droplet signal, calculates the area below the squared voltage signal as the electrical energy consumed in vaporizing the droplet, and from that determines the droplet mass, the electrical energy being equivalent to the requisite quantity of heat supplied to the droplet for heating it to boiling temperature and then completely evaporating it.

2. The method according to claim 1, wherein the number of water droplets striking the measurement probe is limited by the size of the measurement area and by means of a suitable hydrodynamic shaping of the measurement probe body, such that the number of small droplets with a diameter below 20 μm is reduced to a number that is still detectable by the method.

3. The method according to claim 1, wherein the program is is adapted to account for variables of flow temperature, probe geometry, film temperature, droplet rate, and heat dissipation at the probe body.

4. An apparatus for determining the size of airborne water droplets in an oncoming water-droplet-bearing air flow, the droplets having a diameter in the range from 1 to 100 μm and a velocity of from 50 to 150 m/s relative to the apparatus, comprising:

an operating device with an integrated A/D converter;

a measurement probe including a probe body;

a signal processor coupled to the operating device and to the probe;

a quartz disk integrated into the probe body;

a flat platinum film approximately 0.5 μm thick, vapor-deposited onto a film-bearing face of the disk, the film having an area smaller than 1 mm$^2$;

the film-bearing face of the disk and the film thereon being oriented perpendicular to the flow and facing thereto for impact of an oncoming water droplet onto the film-bearing face;

means for keeping a temperature of the film constant at a temperature above 100° C. by means of a bridge circuit in the operating device with a regulating frequency of more than 200 kHz;

means for digitizing an analog voltage output signal of the bridge circuit over predetermined measuring time intervals by means of the A/D converter at a selected frequency from 0.1 to 1 MHz; and means for further processing the digitized output signal of the bridge circuit by means of a computer program of the signal processor which program:

(i) recognizes a signal of an individual impacting droplet and distinguishes the signal of the droplet from signal fluctuations caused by air-flow velocity fluctuations;

(ii) also identifies the signal of a droplet, even if the signal of the droplet that impacted previously has not yet decayed to a baseline value; and (iii) for each droplet signal, calculates the area below the squared voltage signal as the electrical energy consumed in vaporizing the droplet, and from that, the electrical energy being equivalent to the requisite quantity of heat supplied to the droplet for heating it to boiling temperature and then completely evaporating it, determines the droplet mass.

* * * * *